United States Patent [19]

Imran

[11] Patent Number: 4,488,555

[45] Date of Patent: Dec. 18, 1984

[54] BATTERY CONDITION WARNING SYSTEM FOR MEDICAL IMPLANT

[75] Inventor: Mir Imran, Pittsburgh, Pa.

[73] Assignee: Mieczyslaw Mirowski, Owings Mills, Md.

[21] Appl. No.: 449,229

[22] Filed: Dec. 13, 1982

[51] Int. Cl.³ .............................................. A61N 1/36
[52] U.S. Cl. ............................ 128/419 PT; 340/636; 320/48
[58] Field of Search ................... 128/419 PT, 419 D; 340/636; 320/48

[56] References Cited

U.S. PATENT DOCUMENTS

| | | | |
|---|---|---|---|
| 3,927,366 | 12/1975 | Mulier et al. | 320/48 |
| 3,974,441 | 8/1976 | Van Den Haak | 320/48 |
| 4,025,916 | 5/1977 | Arnold et al. | 340/636 |
| 4,119,904 | 10/1978 | Haglund | 320/48 |
| 4,210,149 | 7/1980 | Heilman et al. | 128/419 D |
| 4,251,811 | 2/1981 | Wittlinger | 340/636 |
| 4,287,517 | 9/1981 | Naget | 340/636 |
| 4,313,079 | 1/1982 | Lee | 320/48 |
| 4,345,603 | 8/1982 | Schulman | 128/419 PT |
| 4,445,512 | 5/1984 | Krupka et al. | 128/419 PT |
| 4,448,197 | 5/1984 | Nappholz et al. | 128/419 PT |

FOREIGN PATENT DOCUMENTS 2427817  2/1980  France .......................... 128/419 PT Primary Examiner—William E. Kamm
Assistant Examiner—Mitchell J. Shein
Attorney, Agent, or Firm—Fleit, Jacobson, Cohn & Price

[57] ABSTRACT

A battery condition warning system for use in a battery powered medical implant device which generates an audible alarm to warn the patient of an impending battery failure. The warning system monitors the voltage potential of the battery during operation of the defibrillator, and when the voltage potential falls below a predetermined level, it activates an audible alarm which is heard by the patient. The system further includes a control circuit adaptable to deactivate the audible alarm in response to a first external magnetic condition, to deactivate the timer in response to a second external magnetic condition, or to conduct an internal test in response to a third external magnetic condition.

6 Claims, 1 Drawing Figure

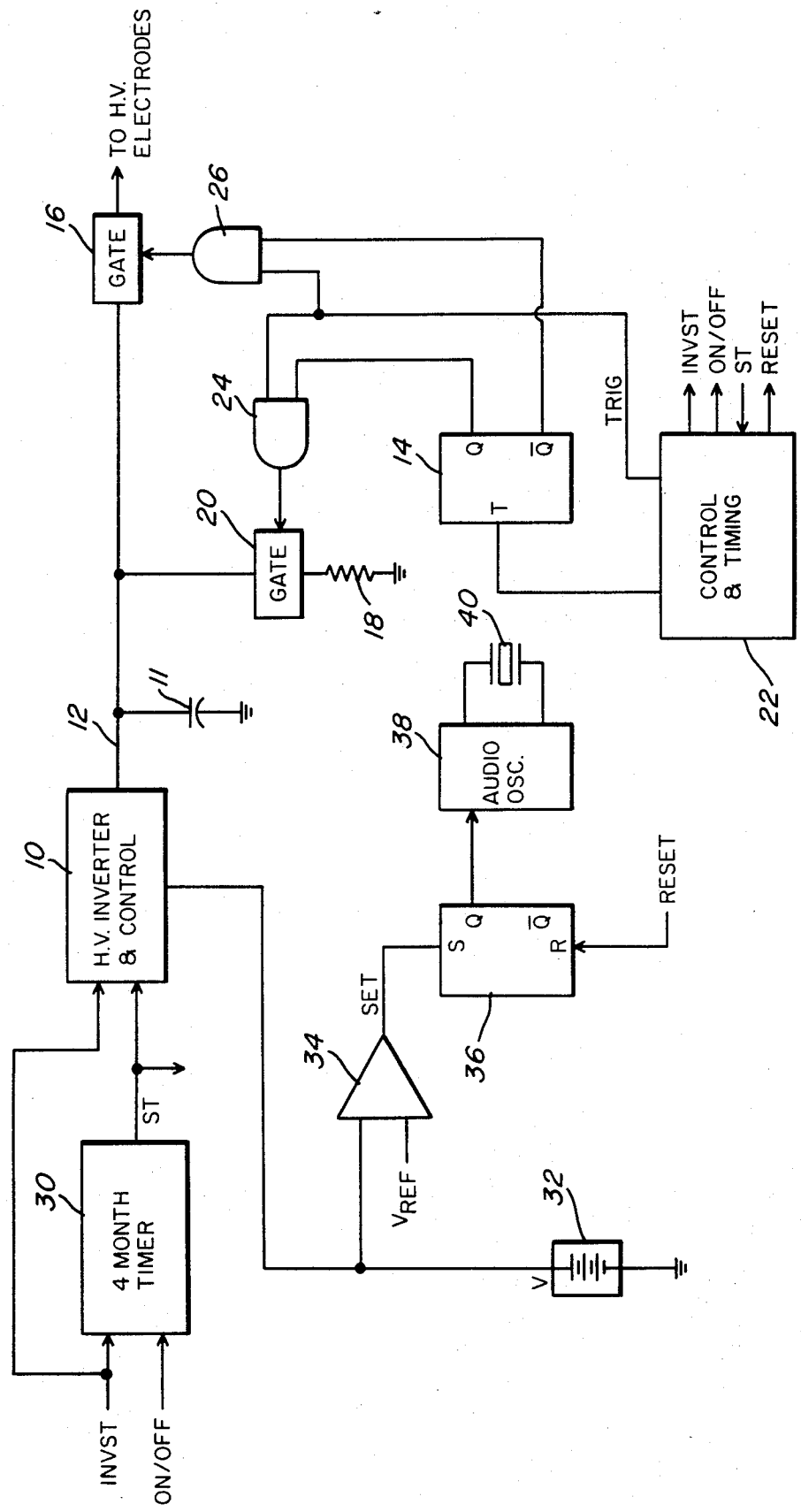

BATTERY CONDITION WARNING SYSTEM FOR MEDICAL IMPLANT

BACKGROUND OF THE INVENTION

This invention pertains to a battery powered medical implanted device, but more specifically, to a self-testing circuit for periodically and automatically testing the battery condition of such a device. Related subject matter can be found in commonly owned U.S. patent application Ser. No. 370,191, abandoned in favor of co-pending U.S. patent application Ser. No. 478,038 entitled Implantable Cardiac Defibrillator Employing Biopolar Sensing and Telemetry Means, incorporated herein.

The aforementioned U.S. patent application illustrates an example of one type of medical device in which this invention may be used. Because many implantable devices, if they are to perform electrical diagnostic and monitoring functions, are battery powered, after a period of time, the battery and/or the device must be surgically replaced, thus requiring the patient to submit to operative procedures. If the medical implant performs a critical life saving function, then it would obviously be of utmost importance to assure failsafe operation, not only of the circuit components which perform the monitoring and diagnostic functions, but also of the storage batteries.

Under current medical practice, battery operated devices are replaced after the passage of a predetermined time period or after performance of a certain number of treating events by the implant. In a standby defibrillator of the type described in above-mentioned U.S. co-pending patent application Ser. No. 478,038, the battery is replaced approximately every three to three and one-half years, or in the case of frequent issuance of high-energy defibrillating pulses, after issuance of about every ninety to one hundred defibrillating pulses. Sometimes, however, good batteries are unnecessarily replaced because their scheduled life, rather than their actual life, have passed, and this obviously presents an inconvenience to the patient. Such unnecessary replacement might result from favorable operating circumstance of the implanted medical device or from an extremely durable battery exceeding its manufacturing design specification. On the other hand, a battery might prematurely fail because it does not meet its intended design specifications, although being tested for such prior to release from its manufacturer. Other circumstances, as well, affect the actual life of the battery.

Thus, to minimize unnecessary surgical operations and/or to prevent premature battery failure, it is a general objective of the present invention to provide a battery condition warning system for use in a medical implanted device which warns the patient of an impending battery failure so that the patient may take remedial action.

Another objective of the present invention is to provide a battery condition warning system operative to test a battery both during the operation of the medical implanted device and at fixed periodic time instances during automatic self-testing cycles of the warning system.

A further objective of the present invention is to provide a battery condition warning system that enables the batteries to be replaced on an as-needed basis, rather than at fixed periodic time instances, thereby to minimize undue surgical replacement of the batteries and to reduce the likelihood of premature battery failure.

SUMMARY OF THE INVENTION

In accordance with this invention, the above-mentioned and further objectives are accomplished by means of a battery condition warning system for use in a battery powered implant having a treating circuit, such as a defibrillator, activated by an event triggering signal to perform a treating function, wherein the warning system comprises a resettable timer that is reset in response to each occurrence of the event triggering signal to restart its timing cycle or that generates, after predetermined periodic time periods, a self-test triggering signal to activate automatically the treating circuit; a control circuit responsive to the self-test signal operative to cause the treating circuit to perform its function internally, rather than to the patient; a monitoring circuit which monitors the state of the battery during the performance of each treating function; and an alarm which notifies the patient of an impending battery failure.

In an illustrative embodiment, the treating circuit comprises a standby cardiac defibrillator which includes a high voltage inverter that issues high-energy defibrillating pulses to the patient's heart. While the high voltage inverter circuit is running, the monitoring circuit monitors the voltage level of the battery during current drain, and if the voltage falls below a certain predetermined level, an alarm is activated. If the treating circuit is not called upon to perform its treating function, the resettable timer automatically and periodically activates the treating circuit at the end of its time-out period, which preferably is four months. Thus, the battery condition warning system of the invention warns the patient of an impending battery failure, preferably by an audio indication, so that the batteries need only be replaced on an as-needed basis. Advantageously, the invention reduces unnecessary operative battery replacement procedures.

Other advantages, features and aspects of the foregoing invention will become more readily apparent upon review of the succeeding disclosure taken in connection with the accompanying drawings. The invention, however, is pointed out with particularity in the appended claims.

BRIEF DESCRIPTION OF THE DRAWINGS

FIG. 1 is a block diagram circuit of a preferred circuit arrangement for carrying out the objectives of this invention.

DESCRIPTION OF ILLUSTRATIVE EMBODIMENT

As previously indicated, the circuit of FIG. 1 is used in connection with an implanted medical device incorporating a treating circuit, such as a high voltage inverter and control circuit 10, which monitors ECG activity of the patient's heart and, in response to detection of a fibrillating condition, issues to the patient's heart high energy defibrillating pulses over a conductor 12. Depending upon the state of the status flip-flop 14, the high-energy pulses pass to the heart by way of high voltage electrodes (not shown) coupled to the patient's heart via a gate 16, or to an internal load resistor 18 via a gate 20. As shown and described in co-pending U.S. patent application Ser. No. 478,038, gates 16 and 20 are silicon-control rectifiers and respond to a TRIG signal from a timing and control circuit 22. When the "Q" output of the status flip-flop 14 is asserted, it enables an AND gate 24 to pass the TRIG signal directly to the control input of the gate 20 thereby to pass the high energy defibrillating pulse to the load resistor 18. On the other hand, if the "$\overline{Q}$" output of the status flip-flop 14 is asserted, then it enables an AND gate 26 to pass the TRIG signal directly to the control input of gate 16 thereby to pass the high energy defibrillating pulses to the electrodes coupled to the patient's heart. These operations are explained in the aforementioned patent application. The foregoing defibrillator circuit is intended to be an illustration of a type of treating device in which the operative elements of this invention may be incorporated.

As part of the battery condition warning system, the timing and control circuit 22 generates an INVST signal to start simultaneously the high voltage inverter and control circuit 10 and a four month resettable timer 30. The INVST signal emanates in response to the detection of an actual fibrillation of the heart or in response to a test condition, such as the magnet test referred to in the above-mentioned related patent application. Activation of the inverter circuit 12 drains a certain amount of power from the battery 32. Since a storage cell 32 has a predictable I-V (current vs. voltage) characteristic, and there exists a corresponding relationship between a point on its I-V curve and the condition (e.g. remaining life) of the battery 32, one can determine the approximate remaining life of the battery 32 by measuring its potential during the period of current drain while the inverter in the circuit 10 is running. A predetermined minimum voltage of the battery 32 during operation of the circuit 10 indicates potential battery failure. To measure battery voltage during this condition, a comparator 34 compares the output voltage of the battery with a REF voltage potential, and produces a SET signal when the voltage "V" falls below $V_{REF}$. The SET signal then sets a flip-flop 36 which activates an audio oscillator 38. Oscillator 38 drives a piezoelectric crystal 40. The piezoelectric crystal 40 causes the system to generate audible sounds which can be heard by the patient thereby informing the patient of potential battery failure.

In the event that the timing and control circuit 22 is not called upon to generate the INVST signal either in response to an actual detection of a fibrillating heart or upon demand by magnet test, then the four month timer circuit 30 times out, sua sponte, and generates self-test activating signal ("ST signal") which activates the high voltage inverter and control circuit 10. The timing and control circuit 22 also receives the ST signal and in response thereto, alters the state of status flip-flop 14 to enable the AND gate 24. Thus, by the time the high voltage capacitor 11 charges, the high energy defibrillating pulse is conditioned to be routed to the test load 18 upon assertion of the TRIG signal by the timing and control circuit 22. For the duration of running of the high voltage inverter in the circuit 10, the comparator 34 again monitors the voltage V and compares it with $V_{REF}$. If V falls below $V_{REF}$, the audio alarm system is activated in a manner previously explained.

The audio oscillator 38 remains activated until reset by a reset signal from the timing and control circuit 22. As explained in the above-mentioned co-pending U.S. patent application, the timing and control circuit 22 is responsive to an external magnet to generate the various control signals. An ON/OFF control signal from the circuit 22 turns off and on the four month timer 30, generates an INVST signal to restart the timer 30 and start the inverter 10, and generates a RESET signal to clear the latch 36. These signals can be generated by various sequences of placement and removal of a magnet about a subcutaneously implanted reed switch to produce associated sequences of signals to effect the desired control. Examples of such circuit arrangements is described in the above-mentioned co-pending U.S. patent application.

It is apparent that various modifications and changes can be made by those skilled in the art without departing from the true scope and spirit of the invention as above described. For example, the crystal 40 may be sounded continuously, or may be switched on and then off, alternately. Further, the crystal can be sounded for short periods of time (such as 30 seconds) at spaced intervals (such as every hour). Accordingly, it is the intent herein to include all such alternate embodiments, variations, and modifications as may come within the true scope of this invention.

What is claimed is:

1. A battery condition warning system in combination with a battery powered medical implant, including a treating circuit activated by an event signal generated in response to the onset of a medical condition or a self-test signal for respectively performing a treating function to a patient or to an internal test load, said system comprising:
   resettable timer means for generating said self-test signal after a predetermined time period, said timer means being reset upon each assertion of said event signal;
   control means responsive to said self-test signal to cause said treating circuit to perform said treating function to said internal test load;
   monitoring means for monitoring the voltage potential of said battery during activation of said treating circuit and for producing an alarm signal when said voltage potential falls below a predetermined level; and
   alarm means responsive to said alarm signal for producing an alarm.

2. A battery condition warning system as recited in claim 1 wherein said alarm means comprises an audio oscillator and a piezoelectric crystal for generating audio signals thereby to warn the patient of impending battery failure.

3. A battery condition warning system as recited in claim 2 wherein said monitoring means comprises a comparator which compares said voltage potential of said battery to a reference voltage, and latch means which responds to said comparator by activating said audio oscillator in response to said comparator, said latch means being reset in response to the assertion of said event signal and said self-test signal.

4. A battery condition warning system as recited in claim 3 wherein said control means further includes means responsive to a first external magnetic condition for activating said treating circuit, means responsive to a second external magnetic condition for resetting said latch to deactivate said audio oscillator, and means responsive to a third external magnetic condition for deactivating said resettable timer means.

5. A battery condition warning system in combination with a battery powered medical implant including an automatic standby defibrillator activated by an event signal generated in response to the detection of fibrillation or a self-test signal thereby to issue a high-energy defibrillating pulse respectively to the heart of a patient or to an internal load resistance, said system comprising:

resettable timer means for generating said self-test signal after a predetermined time period, said timer means being reset upon each assertion of said event signal;

control means responsive to said self-test signal to effect delivery of said high energy defibrillating pulses to said internal load resistance;

monitoring means for monitoring the voltage level of said battery during activation of said defibrillator and for producing an alarm signal when the voltage potential falls below a predetermined level; and alarm means responsive to said alarm signal for generating an audible alarm which warns the patient of an impending battery failure.

6. A battery condition warning system as recited in claim 5 wherein said control means is responsive to a first external magnetic condition to generate said event signal and to effect delivery of said high energy defibrillating pulses to said internal load resistance, means responsive to a second external magnetic condition for deactivating said resettable timer means, and means responsive to a third external magnetic condition for deactivating said audio alarm means.

* * * * *